(12) United States Patent
Kovac et al.

(10) Patent No.: US 11,344,418 B2
(45) Date of Patent: May 31, 2022

(54) MALE PROSTHESIS

(71) Applicants: Jason Kovac, Indianapolis, IN (US);
Richard Wassersug, Vancouver (CA)

(72) Inventors: Jason Kovac, Indianapolis, IN (US);
Richard Wassersug, Vancouver (CA)

( * ) Notice: Subject to any disclaimer, the term of this patent is extended or adjusted under 35 U.S.C. 154(b) by 0 days.

(21) Appl. No.: 16/699,495

(22) Filed: Apr. 23, 2020

(65) Prior Publication Data

US 2020/0315799 A1 Oct. 8, 2020

Related U.S. Application Data

(60) Provisional application No. 62/773,165, filed on Nov. 29, 2018.

(51) Int. Cl.
*A61F 2/26* (2006.01)

(52) U.S. Cl.
CPC ........ *A61F 2/26* (2013.01); *A61F 2230/0069* (2013.01); *A61F 2250/0036* (2013.01)

(58) Field of Classification Search
CPC ............................ A61F 2/26; A61F 2250/0036
See application file for complete search history.

(56) References Cited

U.S. PATENT DOCUMENTS

| 4,392,562 A * | 7/1983 | Burton ...................... A61F 2/26 |
| | | 600/40 |
| 5,512,033 A * | 4/1996 | Westrum, Jr. ............. A61F 2/26 |
| | | 600/139 |
| 2012/0022324 A1* | 1/2012 | Forsell ...................... A61F 2/26 |
| | | 600/40 |

OTHER PUBLICATIONS

Wassersug, R. et al., "Non-pharmacological and non-surgical strategies to promote sexual recovery for men with erectile dysfunction," Translational Andropogy and Urology, vol. 6 Supp. 5, Nov. 2017, S776-S794.

* cited by examiner

*Primary Examiner* — John P Lacyk
(74) *Attorney, Agent, or Firm* — Taft Stettinius & Hollister LLP

(57) ABSTRACT

A male prosthesis applicable for treating male sexual dysfunction. The prosthesis includes a restraining/strengthening region operable to behave similar to a suspensory ligament in the human body.

22 Claims, 5 Drawing Sheets

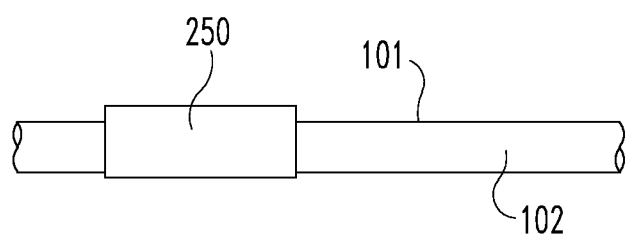 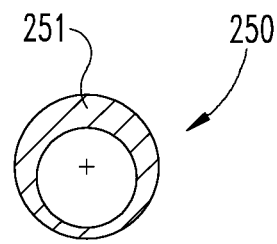
*Fig. 4*        *Fig. 4a*
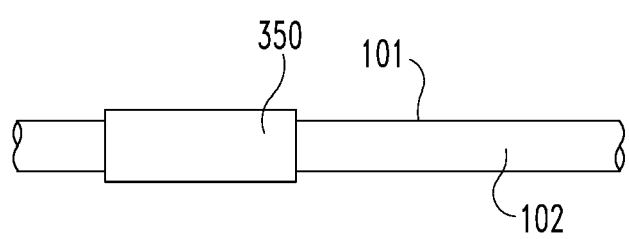 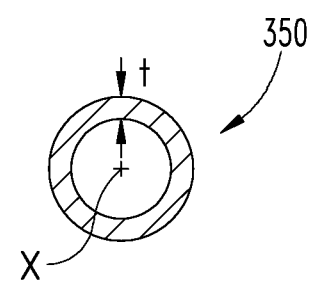
*Fig. 5*        *Fig. 5a*

MALE PROSTHESIS

RELATED APPLICATIONS

The present application claims the benefit of U.S. Provisional Application No. 62/773,165 filed Nov. 29, 2019 which is incorporated herein by reference.

TECHNICAL FIELD

The present application generally relates to implantable and external male prosthetic penis.

BACKGROUND

Sexual dysfunction can happen in men of any age, although it becomes increasingly common as men get older. Erectile dysfunction can affect men's confidence and self-esteem leading to depression, which in turn, can negatively impact men's intimate relationships and quality of life overall. There are currently many medical treatments available for erectile dysfunction including external prosthetics, oral pills and injectable penile medications. When these non-invasive strategies fail, surgical placement of a penile prosthesis remains the gold standard. Presently, there are a few options available for surgical implantation and even fewer for external prosthetics. The devices that are currently being implanted across the world have been around for many decades with few advances made beyond the basics and typically involve minor advancements in the basic components. To date, no advancements have taken into account the male anatomical structure; as is proposed in this application. As such, there remains a significant need for the modifications contained within this application in order to enhance the satisfaction and anatomical appropriateness of penile prosthetics.

SUMMARY

The present application relates generally to male prosthetic systems in implantable and external forms. In one aspect, the systems are configured to include structures that augment and/or replace the function of the suspensory ligament in the male human body. Further embodiments, forms, features, aspects, benefits and advantages of the present application shall become apparent from the description and figures provided.

BRIEF DESCRIPTION OF THE DRAWINGS

The description makes reference to the accompanying drawings wherein like reference numerals refer to like parts throughout the several views, and wherein:

FIG. 4 illustrates one embodiment of the present invention of FIG. 3, including a geometrically non-symmetrical reinforcing region.

FIG. 4a illustrates in cross section one embodiment of the geometrically non-symmetrical reinforcing region.

FIG. 5 illustrates another embodiment of the present invention of FIG. 3 including a geometrically symmetrical reinforcing region.

FIG. 5a illustrates in cross section one embodiment of the geometrically symmetrical reinforcing region.

DETAILED DESCRIPTION OF THE ILLUSTRATIVE EMBODIMENTS

Figure 1:
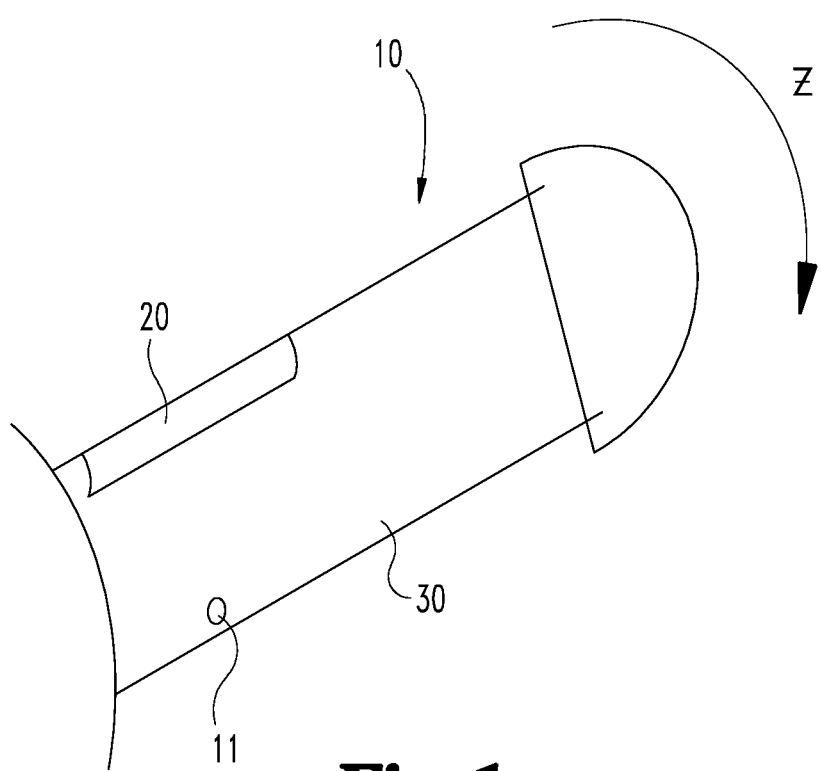
FIG. 1 illustratively depicts an external prosthetic penis in accordance with an embodiment of the present application.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With reference to FIG. 1, there is illustrated one form of an external male prosthesis device 10. The reader should note that the present application is contemplated for both an internal implantable prosthesis device and an external prosthesis device. Prior devices of this general type are readily known to one of ordinary skill in the art and are available in the marketplace. A short coming of the prior devices of this general type is the structure allows for the unrestrained movement/deflection denoted by arrow Z. This unrestrained movement/deflection results in a movement of the device in a direction that is opposite of a desired upward rotation (counterclockwise in FIG. 1) by the shaft 30 of the prosthesis 10. The shaft 30 includes a tip end and a second end disposed at the other end of the elongated shaft. The shaft further includes a top surface and a bottom surface. The document will also in places contemplate the relative movement in an upward and a downward direction. For clarity, the term upward is generally considered to be rotation/movement generally opposite to the direction of arrow Z in FIG. 1, and downward rotation/movement is considered to be rotation/movement substantially in the same direction as arrow Z in FIG. 1.

With continued reference to FIG. 1, there is illustrated in one form of the present application that the shaft includes a modified portion 20. The modified portion 20 is constructed to prevent and/or resist downward rotation/movement (clockwise) in the direction of arrow Z. In one form the present application includes structure to resist an ventral/anterior force The amount of resistance to downward rotation/deflection can be tailored to meet preferred anatomical configurations for a human body. The human body contains a suspensory ligament that functions to stabilize and control motion of the male penis. The present application recognizes that a prosthetic penis, either implantable or external, including structure to address the function of the suspensory ligament is desired and has not been properly contemplated in prior devices/systems. In one form the mechanical properties of the shaft 30 are modified in a local region relative to other portions of the shaft to produce a stiffer area that is resistant to bending in this region. The present application contemplates that a shaft 30 will have mechanical properties tailored to resistant bending that are not uniform along its length.

In yet another form a mechanical strong-back is provided within the structure of shaft 11 in the modified region 20. This mechanical strong-back may take many forms; however its properties of interest focus upon mechanical stiffness and/or torsional stiffness. In a preferred form the mechanical strong-back is integrated with the wall of the shaft 11. Materials for the construction of the external male prosthesis 10 are generally known to one of skill in the art.

The modified region 20 can also be contemplated as a circumferential ring having mechanical properties relative to other portions of the shaft that produce a stiffer area that is resistant to bending and/or rotation in this region but not limited in length along the entirety of the shaft.

In another form of the present invention the prosthesis is an implantable male prosthesis located within the male anatomy. The implantable male prosthesis is preferably one that changes shape based upon the movement of fluid within the implantable male prosthesis system. More specifically the change in shape is related to the corresponding change in the male penis from a flaccid state to an erect/firm state. However, other forms of implantable male prosthesis are contemplated herein (including malleable prosthetics).

Implantable male prosthetic penis systems are generally known to one of skill in the art. As discussed above, short coming of the prior implantable male prosthesis systems of this general type is the system's structure allows for the somewhat unrestrained movement/deflection denoted by arrow Z in FIG. 1. A reader will recognize that the overall system in the implantable versus the non-implantable systems is distinct from one another. However, both types of prior prosthesis systems and devices include issues associated with this unrestrained movement/deflection which result in a movement of the device in a direction that is opposite of a desired upward rotation (counterclockwise in FIG. 1) by the shaft of the prosthesis of the implantable system.

Figure 2:
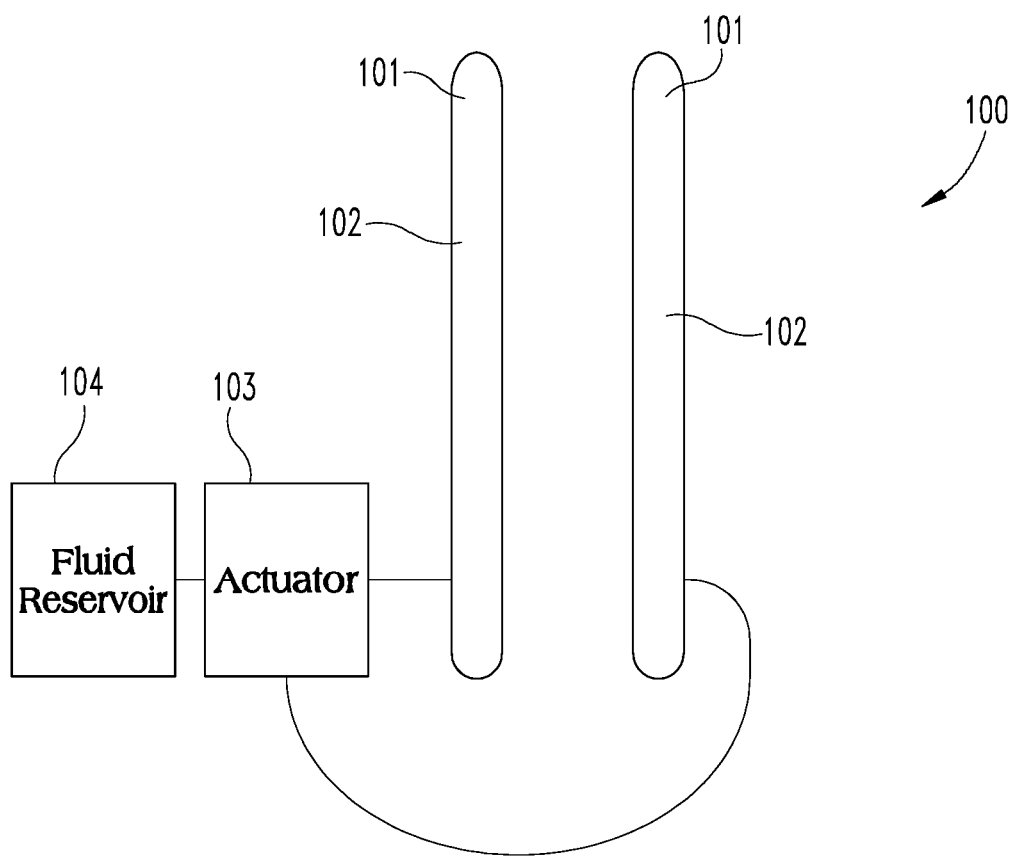
FIG. 2 schematically depicts a plan view of an implantable prosthetic penis.

With reference to FIG. 2, there is schematically illustrated an implantable prosthetic penis system 100. The prosthetic penis system 100 is a closed system that utilizes the movement of a liquid within the system to change the firmness/rigidity of a pair of cylinders 101. The present application further contemplates in an alternate embodiment that the implantable prosthetic penis system includes only one cylinder For the avoidance of doubt the reservoir 104, actuator/control valve 103 and the pair of cylinders 101 are in fluid communication and the system is closed in that fluid is not intended to enter or leave the system. While the pair of cylinders have been called a cylinder they may be a geometric cylinder shape in one embodiment, however other shapes are also contemplated herein. The pair of cylinders in one form are configured of a plyable material that changes shape and/or firmness when the volume of fluid is changed therein. Further, the system is contemplated to not have a phase change in the states of the fluids therein; the only change contemplated is the movement of fluid location within the system to change the physical firmness of the pair of cylinders 101.

Another embodiment of the present application contemplates a malleable prosthetic system including a pair of cylinders functioning without a liquid working fluid, without the fluid reservoir 104 and without a actuator/control valve 103. In the case of a malleable prosthetic system, the cylinders 101 consist of a bendable core without fluid. They are constantly rigid and moved up and down in the Z plane described in FIG. 1.

The cylinders 101 are designed to have a first state that corresponds to a flaccid state of a human penis and a non-flaccid state that corresponds to an erect state of a human penis. The change in state is directly related to the volume of liquid contained in the cylinders 101. The cylinders include an internal volume 102 that is in fluid communication with the actuator/control valve 103 and the fluid reservoir 104. A portion of the liquid within the closed system is moveable between the fluid reservoir 104 and the cylinders 101. The actuator/control valve is operable to allow movement of the liquid within the system. When the actuator/control valve 103 is switched to an open position and actuator is manipulated a portion of the liquid within the closed system is forced into the pair of cylinders 101 to increase the firmness of the cylinders 101.

Figure 3:
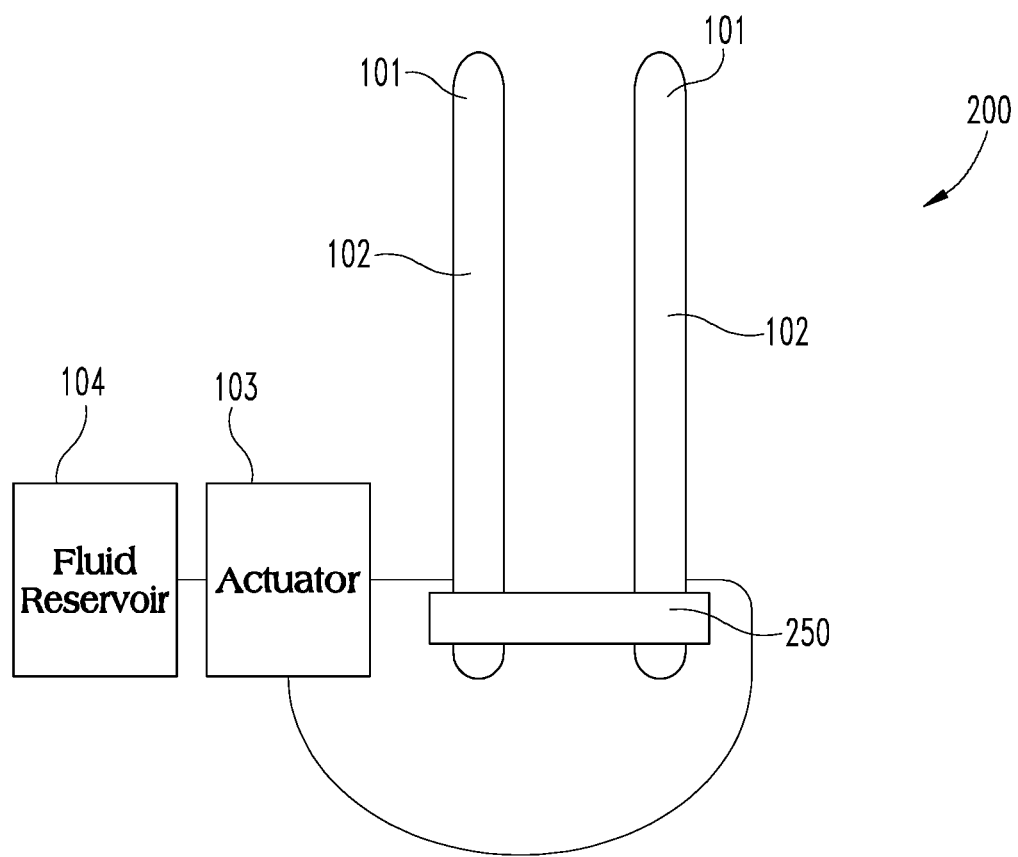
FIG. 3 schematically depicts a plan view of an implantable prosthetic penis of one embodiment of the present application.

With reference to FIG. 3, there is illustrated one embodiment of the prosthetic penis system 200. The prosthetic penis system 200 comprises the elements of the prosthetic system 100 plus a restraining/strengthening region 250. The restraining/strengthening region is preferably located dorsally, laterally and medially in a specific region of, or along the course of, the penile shaft based upon the judgment of the attending physician. This will help to prevent downward deflection and rotation in the direction of z in FIG. 1. The restraining/strengthening region(s) may be designed and integrated into the wall structure of the cylinders 101 or may be an additional structure coupled to the cylinders 101. The restraining/strengthening region is contemplated as spanning an arc less than 360 degrees of the circumference of the wall. In one non limiting form the restraining/strengthening region is defined in an arc having a range between 60 degrees and 140 degrees. Local changes in the material properties and actual wall thickness of the wall of the pair of cylinders are contemplated as one way but not the only way to obtain a restraining/strengthening region. Irrespective of the specific design for the restraining/strengthening region they function to provide a desired resistance and/or limit to movement including but not limited to bending, deflection and/or rotation of the penis in a non-flaccid state as discussed above with the prosthetic penis system 200 implanted. The axial length of the restraining/strengthening region and the associated girth thereof are contemplated to be selectable by the medical professional to meet the needs of the patient.

In one form of the present application the pair of cylinders include locating features spaced along the axial direction of each of the pair of cylinders that will correspond with a locking feature on the restraining/strengthening region. These locating features and locking features correspond to one another and can be engaged to lock the in place at predefined locations. The present application further contemplates that restraining/strengthening region(s) can be a designed and used to interrelate with each of the pair of cylinders individually or with the pair of cylinders together.

With reference to FIGS. 4 and 4a, there is illustrated one embodiment of the restraining/strengthening region 250. In one non-limiting embodiment, the restraining/strengthening region is located on each of a pair of cylinders 101 and is non geometrically symmetrical with a larger reinforced section 251 that corresponds with a portion of the circumference of the wall of the pair of cylinders 101. However, another embodiment of the present application contemplates that the restraining/strengthening region is only located on one of the cylinders and in another embodiment is located on both cylinders but the structure and properties differ between the cylinders. The larger reinforced section may take on a variety of geometries and also may have mechanical material properties that are different from other parts of the restraining/strengthening region 250. The function of the restraining/strengthening region 250 is to replace and or augment the function of the suspensory ligament within the human body. The degree of enhanced coverage of the circumference can be varied based upon a medical professional's assessment of the patient's anatomy. Location for placement could be contemplated to attach to components of the currently available device.

With reference to FIGS. 5 and 5*a* there is illustrated an alternate embodiment of a restraining/strengthening region 350. This non-limiting embodiment is located on the pair of cylinders 101 and is geometrically symmetrical about a centerline X with a thickness 't'. As discussed above the restraining/strengthening regions may be located on one or both of the cylinders and may be identical or differ between the cylinders. The restraining/strengthening region 350 may take on a variety of thicknesses and also may have mechanical material properties that are different around its circumferential regions to obtain a desired resistance to movement including but not limited to bending, deflection and/or rotation of the penis in a non-flaccid state as discussed above with the prosthetic penis system 200 implanted. The function of the restraining/strengthening region 350 is to replace and or augment the function of the suspensory ligament within the human body.

The prosthetic penis system 100 is designed to be biocompatible with the human anatomy and to be permanently placed with the body by surgical techniques. The surgical techniques are not discussed herein as they are well known to physicians and other medical experts that routinely perform this type of surgery. The pair of cylinders 101 are surgically disposed into lumens (corpora cavernosa) within the male penis and the reservoir 104 and actuator/control valve 103 are located at appropriate locations within the human anatomy. A person of skill in the art will recognize that the actuator/control valve 103 must be able to be manipulated from outside the human body to allow the system to be controlled in systems where the transfer of liquid is required. The present embodiments provides for advancements to the malleable, or inflatable, prosthetic cylinders to more appropriately resemble the natural human anatomy/suspensory ligament and thus, more accurately represent the anatomical resistance to rotation/deflection/torsion of the penis to external forces.

Figure 6A:
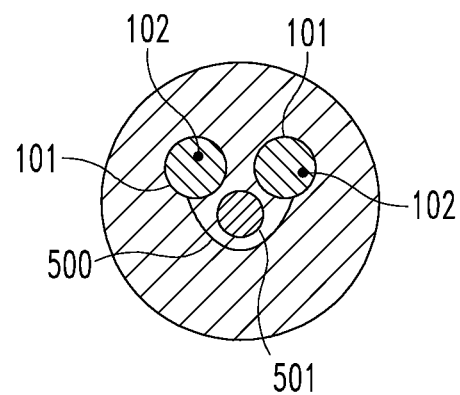
FIG. 6a depicts an illustrative view of the implantable penile prosthetic of FIG. 6 in cross section and further including a support structure for the urethra.
Figure 6:
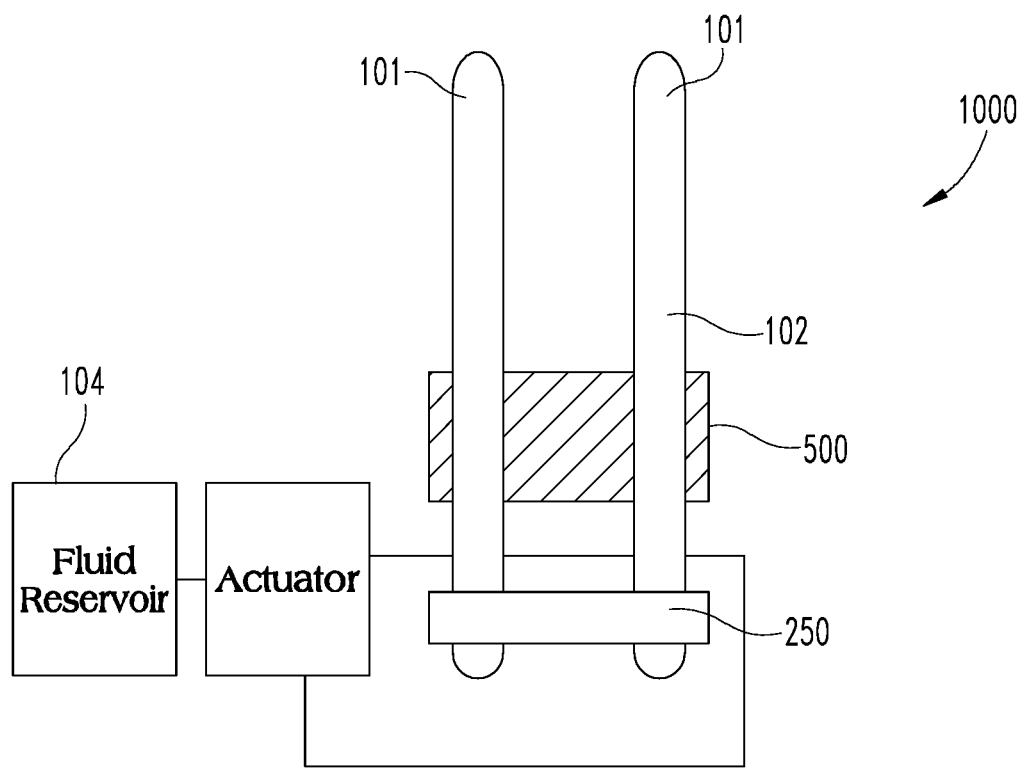
FIG. 6 illustrates the embodiment of FIG. 3 further including a support structure on the bottom side of cylinders.

With reference to FIGS. 6 and 6*a* there is illustrated a further embodiment substantially identical to the embodiment of FIG. 3. The prosthetic penis system 1000 is substantially identical to prior prosthetic penis system 200. Like feature numbers between the systems represent like features. The prosthetic penis system 1000 further includes a support structure 500 coupled to the pair of cylinders 101 and located beneath the bottom surface thereof. The support structure 500 can also be utilized with the previously described system that utilizes a pair of malleable cylinders. The support structure is utilized to support the urethra 501 when placed within the body. The support structure 500 can take a variety of forms including but not limited to a mesh.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

What is claimed is:

1. An implantable penile prosthetic, comprising:
   a closed fluid flow system including a pair of cylinders, a fluid flow reservoir, a fluid flow control and an actuator disposed in fluid communication with one another, the closed fluid flow system compatible with being implanted within the human body;
   each of the pair of cylinders including an interior volume configured for receiving a liquid, the pair of cylinders having a first soft phase and a second firm phase;
   the fluid reservoir having an internal volume for holding at least portion of the liquid;
   the fluid flow control operable for allowing at least a portion of the liquid to flow between the pair of cylinders and the reservoir;
   an actuator operable to cause at least a portion of the liquid within the reservoir to flow into the interior volume of the pair of cylinders, the flow of liquid into the pair of cylinders causes the shift from the first phase to the second phase; and
   a movement limiting element attached with at least one of the pair of cylinders to reduce rotation and or bending of the implantable penis prosthetic when implanted in the human body.

2. The implantable penis prosthetic of claim 1, wherein the movement limiting element reduces rotation and or bending of the implantable penis prosthetic when implanted in a direction away from the stomach of the human body and resists a ventral/anterior force.

3. The implantable penis prosthetic of claim 1, wherein each of the pair of cylinders includes a wall, and wherein the movement limiting element is formed within a portion of the wall of the at least one of the pair of cylinders.

4. The implantable penis prosthetic of claim 1, wherein each of the pair of cylinders includes a wall, and wherein the movement limiting element is coupled with a portion of the wall of the at least one of the pair of cylinders.

5. The implantable penis prosthetic of claim 1, wherein each of the pair of cylinders includes a proximal end and a distal end, the distal end when implanted in a human body is located the furthest distance from the body, and wherein the movement limiting element is located closer to the proximal end than the distal end.

6. The implantable penis prosthetic of claim 3, wherein the movement limiting element is not geometrically symmetrical and is formed in the wall over an axial length and in an arc segment of the wall, the arc segment of the movement limiting element is less than the entire circumference of the wall.

7. The implantable penis prosthetic of claim 6, wherein the arc segment is in a range between 60 degrees and 140 degrees of the 360 degrees of the circumference of the wall.

8. The implantable penis prosthetic of claim 1, wherein the movement limiting element attached with at least one of the pair of cylinders has first material properties and the at least one of the pair of cylinders has second material properties, wherein the first material properties are different from the second material properties.

9. The implantable penis prosthetic of claim 3, wherein the movement limiting element includes a region having a thickness greater than the thickness of the portion of the wall.

10. The implantable penis prosthetic of claim 6, wherein the movement limiting element includes a radially thickened portion.

11. The implantable penis prosthetic of claim 2, wherein the movement limiting element reduces rotation and bending of the implantable penis prosthetic when implanted in a direction away from the stomach of the human body;
wherein each of the pair of cylinders includes a wall, and wherein the movement limiting element is formed within a portion of the wall of the at least one of the pair of cylinders;
wherein each of the pair of cylinders includes a proximal end and a distal end, the distal end when implanted in a human body is located the furthest distance from the body, and wherein the movement limiting element is located closer to the proximal end than the distal end; and
wherein the movement limiting element includes at least one of a radially thickened portion and a portion having a material property that is different than a material property of the wall.

12. The implantable penis prosthetic of claim 11, wherein the movement limiting element is not geometrically symmetrical and is formed in the wall over an axial length and in an arc segment of the wall, the arc segment of the movement limiting element is less than the entire circumference of the wall.

13. The implantable penis prosthetic of claim 2, wherein the movement limiting element reduces rotation and bending of the implantable penis prosthetic when implanted in a direction away from the stomach of the human body;
wherein each of the pair of cylinders includes a wall, and wherein the movement limiting element is coupled with a portion of the wall of the at least one of the pair of cylinders;
wherein the movement limiting element attached with at least one of the pair of cylinders has first material properties and the at least one of the pair of cylinders has second material properties, wherein the first material properties are different from the second material properties; and
wherein the movement limiting element is defined by an arc segment having a thickened portion with a thickness greater than the rest of movement limiting element extending around at least a portion of the circumference of the at least one cylinder.

14. An implantable penis prosthetic, comprising:
a closed fluid flow system including a pair of cylinders, a fluid flow reservoir, a fluid flow valve and an actuator disposed in fluid communication with one another;
each of the pair of cylinders including an interior volume configured for receiving a liquid, the pair of cylinders having a first phase and a second phase;
the fluid reservoir having an internal volume for holding at least portion of the liquid;
the fluid flow valve operable for controlling the passage of the liquid between the pair of cylinders and the reservoir;
an actuator operable to cause at least a portion of the liquid within the reservoir to flow into the interior volume of the pair of cylinders, the flow of liquid into the pair of cylinders causes the shift from the first phase to the second phase, wherein the second phase has a firm configuration; and
a restraint associated with the pair of cylinders to reduce rotation and or bending of the implantable penis prosthetic when implanted in the human body.

15. The implantable penis prosthetic of claim 14, wherein the restraint when the implantable penis prosthetic is implanted in a human and functions to augments the suspensory ligament of the human.

16. The implantable penis prosthetic of claim 14, wherein the restraint is formed in a wall of each of the pair of cylinders.

17. The implantable penis prosthetic of claim 14, wherein the restraint is connected with a wall of each of the pair of cylinders.

18. The implantable penis prosthetic of claim 14, wherein the restraint is connected with a material that while functioning to connect the pair of cylinders thus resisting torsion/bending while also located in such a way to support the urethra and assist urinary continence by applying pressure on the urethra/corpus spongiosum.

19. A male penis prosthesis, comprising:
a shaft structure having an elongated structure with a tip disposed at a first end and a second end;
wherein the shaft structure has stiffness characteristics along the length of the shaft structure, wherein the stiffness characteristics are not uniform along the shaft structure; and
wherein a portion of the shaft structure has stiffness characteristics that resist bending and or rotation of the shaft structure in a substantially downward direction, the portion is located closer to the second end.

20. The male prosthesis of claim 19, wherein the prosthesis is part of an implantable penis prosthetic system.

21. The male prosthesis of claim 19, wherein the portion of the shaft is configured to provide resistance to downward rotation analogous to a suspensory ligament in a male human body; and
wherein the shaft is not formed of a rigid non-flexible material.

22. An implantable penis prosthetic, comprising:
a malleable device with pair of cylinders that are malleable and functioning to support the human penis;
a restraint associated with the pair of cylinders to reduce rotation and or bending of the implantable penis prosthetic when implanted in the human body.

* * * * *